(12) United States Patent
Donhowe et al.

(10) Patent No.: US 11,443,501 B2
(45) Date of Patent: Sep. 13, 2022

(54) ROBOTIC SURGICAL SAFETY VIA VIDEO PROCESSING

(71) Applicant: Verily Life Sciences LLC, South San Francisco, CA (US)

(72) Inventors: Caitlin Donhowe, Mountain View, CA (US); Joëlle Barral, Mountain View, CA (US); Xing Jin, San Jose, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 374 days.

(21) Appl. No.: 16/694,223

(22) Filed: Nov. 25, 2019

(65) Prior Publication Data

US 2020/0184248 A1    Jun. 11, 2020

Related U.S. Application Data

(60) Provisional application No. 62/775,501, filed on Dec. 5, 2018.

(51) Int. Cl.
  *A61B 34/30* (2016.01)
  *G06V 10/20* (2022.01)
  (Continued)

(52) U.S. Cl.
  CPC ............ *G06V 10/255* (2022.01); *A61B 34/20* (2016.02); *A61B 34/25* (2016.02); *A61B 34/37* (2016.02);
  (Continued)

(58) Field of Classification Search
  CPC ......... A61B 34/00; A61B 34/20; A61B 34/30; A61B 34/37; A61B 34/25; A61B 19/201;
  (Continued)

(56) References Cited

U.S. PATENT DOCUMENTS 5,983,126 A * 11/1999 Wittkampf ............... A61B 5/06
                                                    600/509
6,863,650 B1    3/2005 Irion
              (Continued)

FOREIGN PATENT DOCUMENTS

WO     2014138916     9/2014
WO     2016014385     1/2016

OTHER PUBLICATIONS

PCT/US2019/063300, "Invitation to Pay Additional Fees and, Where Applicable, Protest Fee", Feb. 28, 2020, 15 pages.
(Continued)

*Primary Examiner* — Vi X Nguyen
(74) *Attorney, Agent, or Firm* — Kilpatrick Townsend & Stockton LLP

(57) ABSTRACT

One example method for improving robotic surgical safety via video processing includes identifying, during a robotic surgical procedure, one or more surgical tools using one or more images of the surgical procedure captured by a camera, the robotic surgical procedure employing a robotic surgical device controlling the one or more identified surgical tools; predicting, for at least one of the one or more images, one or more loaded surgical tools that are controlled by the robotic surgical device and should be in a field of view of the camera; comparing the one or more identified surgical tools with the one or more loaded surgical tools; determining that at least one of the one or more loaded surgical tools does not match any of the one or more identified surgical tools; and causing the at least one loaded tool of the robotic surgical device to be disabled.

17 Claims, 8 Drawing Sheets

(51) Int. Cl.
*A61B 34/37* (2016.01)
*A61B 90/00* (2016.01)
*A61B 34/00* (2016.01)
*A61B 34/20* (2016.01)

(52) U.S. Cl.
CPC ............ *A61B 90/361* (2016.02); *A61B 90/37* (2016.02); *A61B 2034/2065* (2016.02); *A61B 2090/371* (2016.02); *G06V 2201/034* (2022.01)

(58) Field of Classification Search
CPC ... A61B 19/203; A61B 19/5244; A61B 90/00; A61B 90/37; A61B 90/361
See application file for complete search history.

(56) References Cited

U.S. PATENT DOCUMENTS

| | | |
|---|---|---|
| 7,824,328 B2 | 11/2010 | Gattani et al. |
| 2009/0088773 A1 | 4/2009 | Zhao et al. |
| 2009/0317002 A1 | 12/2009 | Dein |
| 2013/0172902 A1* | 7/2013 | Lightcap ................ A61B 34/30 606/130 |
| 2017/0352164 A1 | 12/2017 | Simonovsky et al. |

OTHER PUBLICATIONS

International Application No. PCT/US2019063300, International Search Report and Written Opinion, dated Jul. 8, 2020, 20 pages.

\* cited by examiner

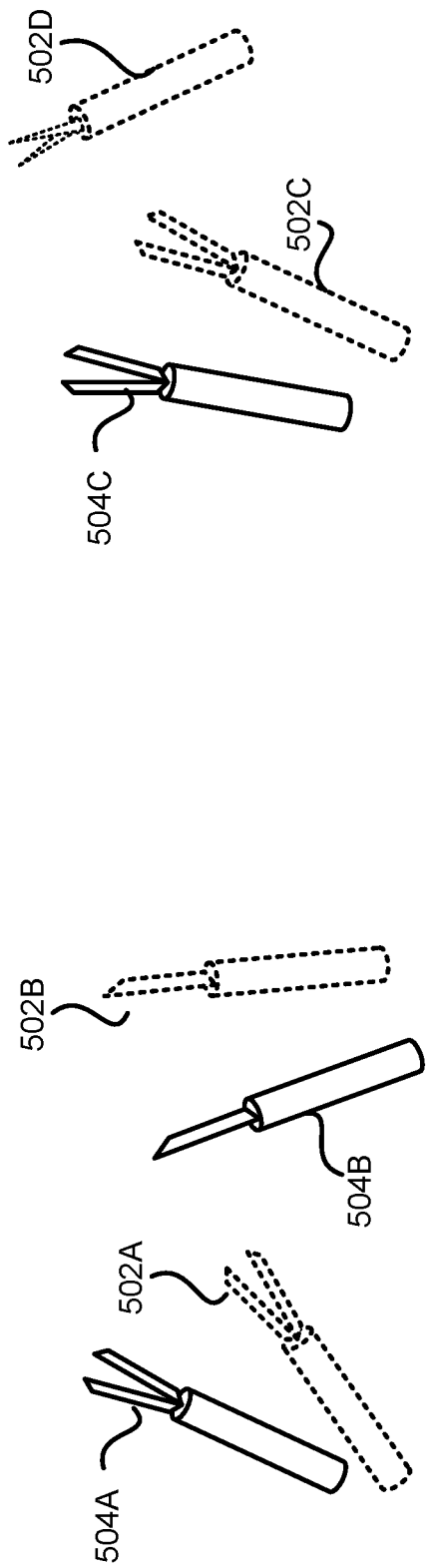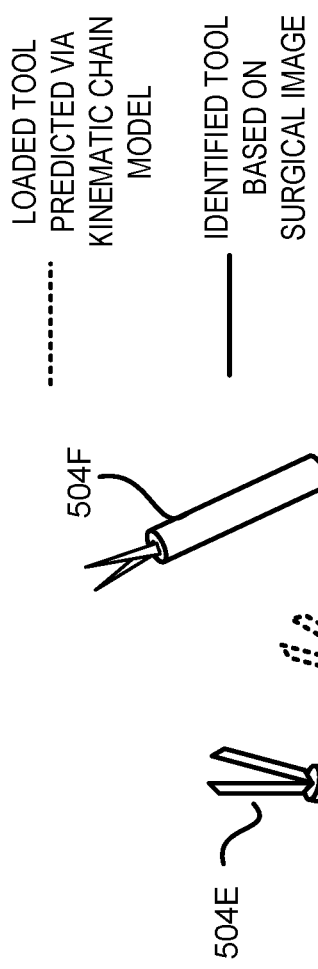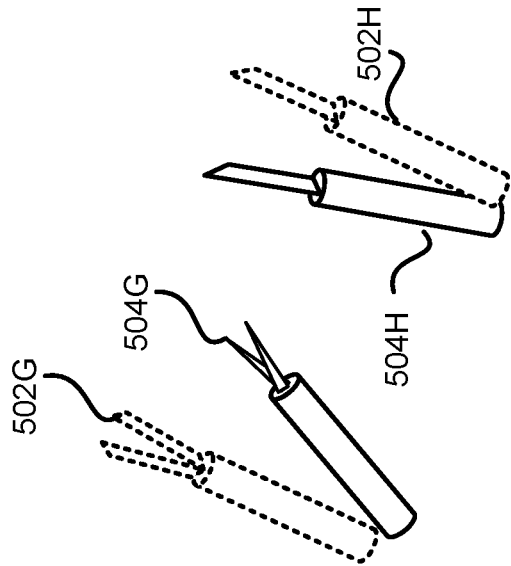

ROBOTIC SURGICAL SAFETY VIA VIDEO PROCESSING

CROSS-REFERENCE TO RELATED APPLICATIONS

This application claims priority to U.S. Patent Application No. 62/775,501, filed Dec. 5, 2018, titled "Robotic Surgical Safety via Video Processing," the entirety of which is hereby incorporated by reference.

FIELD

The present application generally relates to robotic surgery and video processing, and more particularly relates to improving the safety of robotic surgery using video processing.

BACKGROUND

Robotic surgeries are becoming increasingly popular nowadays because of their advantages over the traditional human-operated open surgeries. Surgical tools utilized in robotic surgeries have improved levels of dexterity over a human surgeon. These tools can provide the surgeon maximum range of motion and precision. In addition, high-definition cameras associated with the surgical tools can provide a better view of the operating site to the surgeon than human eyes can provide. Further, the small size of the robotic surgical tools allows the surgeries to be done in a minimally invasive manner thereby causing less trauma on the patient's body.

To ensure safety during a surgery, it is important for a surgeon to be able to visually monitor the surgical tools he is using. However, it is a non-trivial task to calculate the positions of the surgical tools relative to the camera, considering that the surgical tools and the camera are typically attached to the distal ends of long, semi-rigid robot arms. Small deflections or errors in joint measurements can become relatively large errors in predicted tool positions. Additionally, even if the tools are within the camera view and visible to the surgeon, because there is no haptic feedback from the surgical tools to the surgeon, it is possible for the surgeon to inadvertently apply too much force to patient anatomy without realizing it, causing unintentional injury to the patient.

SUMMARY

Various examples are described for improving robotic surgical safety via video processing. One example method includes identifying, during a robotic surgical procedure, one or more surgical tools using one or more images of the surgical procedure captured by a camera, the robotic surgical procedure employing a robotic surgical device controlling the one or more identified surgical tools; predicting, for at least one of the one or more images, one or more loaded surgical tools that are controlled by the robotic surgical device and should be in a field of view of the camera; comparing the one or more identified surgical tools with the one or more loaded surgical tools; determining that at least one of the one or more loaded surgical tools does not match any of the one or more identified surgical tools; and causing the at least one loaded tool of the robotic surgical device to be disabled.

Another method includes identifying a surgical tool used by a robotic surgical device in a surgical procedure using one or more images of the surgical procedure; estimating a pose of the surgical tool based, at least in part, upon the one or more images; determining a difference between the estimated pose of the surgical tool and a predicted pose of the surgical tool predicted through a kinematic chain model of the robotic surgical device; calculating a force exerted by the surgical tool based, at least in part, upon the difference of the estimated pose and predicted pose of the surgical tool; determining that the force is higher than a threshold; and causing the force of the surgical tool to be reduced.

One example robotic surgical device includes a processor; a camera; and a non-transitory computer-readable medium having processor-executable instructions stored thereupon, which, when executed by the processor, cause the processor to: identify, using one or more images of a surgical procedure captured by the camera during a robotic surgical procedure, one or more surgical tools used in the surgical procedure; predict, for at least one of the one or more images, one or more loaded surgical tools that are loaded during the surgical procedure and should be in a field of view of the camera; compare the one or more identified surgical tools with the one or more loaded surgical tools; determine that at least one of the one or more loaded surgical tools does not match any of the one or more identified surgical tools; and cause the at least one loaded surgical tool of the robotic surgical device to be disabled.

An example non-transitory computer-readable medium comprising processor-executable instructions to cause a processor to identify, during a robotic surgical procedure, one or more surgical tools using one or more images of the surgical procedure captured by a camera, the robotic surgical procedure employing a robotic surgical device controlling the one or more identified surgical tools; predict, for at least one of the one or more images, one or more loaded surgical tools that are controlled by the robotic surgical device and should be in a field of view of the camera; compare the one or more identified surgical tools with the one or more loaded surgical tools; determine that at least one of the one or more loaded surgical tools does not match any of the one or more identified surgical tools; and cause the at least one loaded surgical tool of the robotic surgical device to be disabled.

Another example non-transitory computer-readable medium comprising processor-executable instructions to cause a processor to identify a surgical tool used by a robotic surgical device in a surgical procedure using one or more images of the surgical procedure; estimate a pose of the surgical tool based, at least in part, upon the one or more images; determine a difference between the estimated pose of the surgical tool and a predicted pose of the surgical tool predicted through a kinematic chain model of the robotic surgical device; calculate a force exerted by the surgical tool based, at least in part, upon the difference of the estimated pose and predicted pose of the surgical tool; determine that the force is higher than a threshold; and cause the force of the surgical tool to be reduced.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 5A-D show examples of simulated images for matching identified surgical tools with loaded surgical tools to identify safety issues associated with the robotic surgical device;

DETAILED DESCRIPTION

Figure 1:
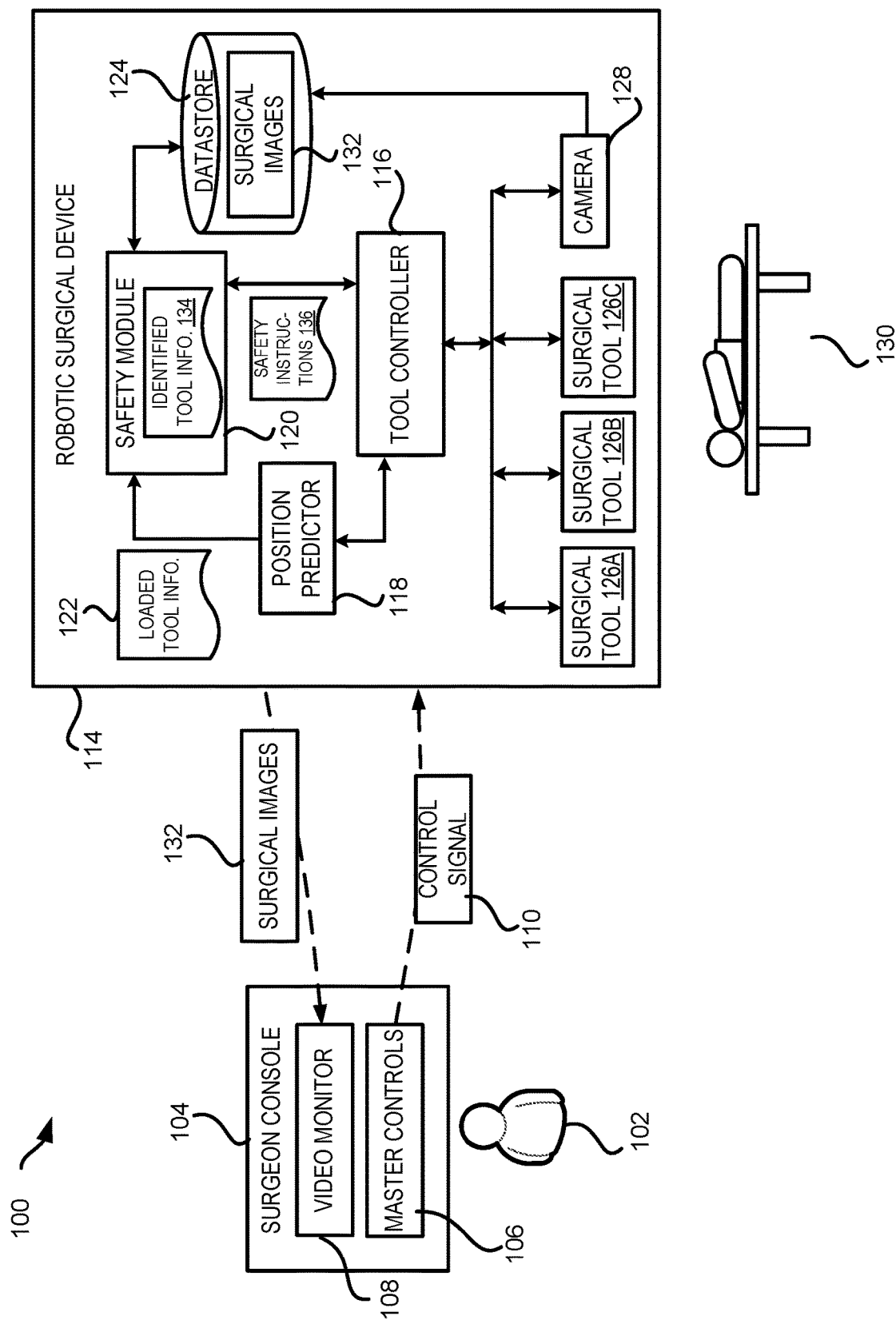
FIG. 1 shows an example of a robotic surgery system with improved safety via video processing.

Examples are described herein in the context of improving robotic surgical safety via video processing. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example of a robotic surgery system with improved safety via video processing, one or more surgical tools are loaded by a robotic surgical device using respective robotic arms. A surgeon can operate these surgical tools through controls at a surgeon console. A camera is also loaded by the robotic surgical device to capture images or videos of a surgical procedure performed using the loaded surgical tools.

The position of a loaded surgical tool relative to the camera can be predicted using a kinematic model of the robotic arm holding the surgical tool and a kinematic model of the robotic arm holding the camera. This relative position can be utilized to determine whether a certain loaded tool is in the field of view of the camera. If so, it means that the surgeon can see the loaded tool in camera and thus it should be enabled to allow the surgeon to use it. If the loaded surgical tool is predicted to be outside the camera view, it would be unsafe to allow the surgeon to use it and thus it should be disabled.

The technology presented herein improves the safety of the robotic surgery system by adding an additional mechanism for identifying the position of the surgical tool and by estimating the force exerted by the surgical tool based on the estimated tool position. Predicting the location of a surgical tool solely based on a kinematic analysis may be insufficient or inaccurate in some cases because various factors can cause a calculated surgical tool position to be incorrect, such as compliance within one or more joints, sensor tolerances within the kinematic chain, external forces applied at one or more locations along the kinematic chain that deflect a member of the chain, etc. Thus, examples according to this disclosure employ image analysis in addition to modelling a kinematic chain to determine whether a loaded surgical tool is within a camera's field of view. In particular, apart from predicting the positions of loaded tools using the kinematic chain model of the robotic surgical device, the positions of the loaded surgical tools can also be estimated by using videos of the surgical procedure captured by the camera. Images captured during a surgical procedure can be analyzed to identify surgical tools that are in the field of view of the camera. The identification can include detecting the positions, poses, and types of the surgical tools captured in the surgical images. The information about the identified surgical tools can then be compared with the information of the loaded surgical tool(s) predicted to be in the camera's field of view through the kinematic models at the time the surgical images are captured to identify any discrepancies, any excessive forces applied by the surgical tool(s), or other safety issues.

As used herein, surgical tools that are identified from the images are referred to as "identified surgical tools" or "identified tools" and the positions of the identified surgical tools estimated based on the images are referred to as "identified positions." Surgical tools that are determined to be in the camera's field of view based on the kinematic chain models are referred to herein as "loaded tools" and the positions of the loaded tools predicted through the kinematic chain models are referred to as "predicted positions."

In one implementation, the positions of the identified surgical tools are compared with the predicted positions of the loaded surgical tools to determine a one-to-one correspondence between the identified surgical tools and the loaded surgical tools. It can then be determined whether the number of identified surgical tools in the surgical images is the same as the number of the loaded surgical tools. If they are different, then the loaded surgical tools that are predicted to be in the camera view but are not detected in the surgical images should be disabled. On the other hand, surgical tools that are predicted to be outside the camera view, but are detected in the surgical images should be enabled.

For the surgical tools that have a one-to-one correspondence between the loaded surgical tools and the identified surgical tools, the type of a loaded surgical tool can be compared with the type of its corresponding identified surgical tool. If the types of the two tools are different, then the surgical tool might be loaded erroneously and should be disabled. If the types of the two tools are the same, a difference between the positions and poses of the two tools in a three-dimensional space can be calculated to estimate the force exerted by the surgical tool. The estimated tool force can be compared with a force threshold to determine if excessive force has been applied by the surgical tool. If so, a warning message can be generated to notify the surgeon to reduce the tool force.

This illustrative example is given to introduce the reader to the general subject matter discussed herein and the disclosure is not limited to this example. The following sections describe various additional non-limiting and nonexhaustive examples and examples of improving robotic surgical safety via video processing.

Referring now to FIG. 1, FIG. 1 shows an example robotic surgical system 100 with improved safety via video processing. The robotic surgical system 100 can include a robotic surgical device 114 configured to operate on a patient 130. The robotic surgical system 100 can also include a surgeon console 104 connected to the robotic surgical device 114 and configured to be operated by a surgeon 102 in order to control and monitor the surgeries performed by the robotic surgical device 114. The robotic surgical system 100 might include additional stations (not shown in FIG. 1) that can be used by other personnel in the operating room, for example, to view surgery information, video, etc., sent from the robotic surgical device 114. The robotic surgical device 114, the surgeon console 104 and other stations can be connected directly or through a network, such as a local-area network ("LAN"), a wide-area network ("WAN"), the Internet, or any other networking topology known in the art that connects the robotic surgical device 114, the surgeon console 104 and other stations.

The robotic surgical device 114 can be any suitable robotic system that can be used to perform surgical procedures on a patient. A robotic surgical device 114 may have one or more robotic arms connected to a base. The robotic arms may be manipulated by a tool controller 116, which may include one or more user interface devices, such as joysticks, knobs, handles, or other rotatable or translatable devices to effect movement of one or more of the robotic arms. The robotic arms may be equipped with one or more surgical tools to perform aspects of a surgical procedure. For example, the robotic arms may be equipped with surgical tools 126A-126C, (which may be referred to herein individually as a surgical tool 126 or collectively as the surgical tools 126). The surgical tools 126 can include, but are not limited to, tools for grasping for holding or retracting objects, such as forceps, graspers and retractors, tools for suturing and cutting, such as needle drivers, scalpels and scissors, and other tools that can be used during a surgery. Each of the surgical tools 126 can be controlled by the surgeon 102 through the surgeon console 104 and the tool controller 116.

In addition, the robotic surgical device 114 may be equipped with one or more cameras 128, such as an endoscope camera, configured to provide a view of the operating site to guide the surgeon 102 during the surgery. In some examples, the camera 128 can be attached to one of the robotic arms of the robotic surgical device 114 controlled by the tool controller 116 as shown in FIG. 1. In other examples, the camera 128 can be attached to a mechanical structure of the robotic surgical device 114 that is separately from the robotic arms.

Different robotic surgical devices 114 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one robotic surgical device 114 is depicted, any suitable number of robotic surgical devices may be employed within a robotic surgical system 100.

In some examples, robotic surgical devices (or a respective controller) may be configured to record data during a surgical procedure. For example, images and videos of the surgical procedures performed by the robotic surgical device 114 can also be recorded and stored for further use. For instance, a datastore 124 can be employed by the robotic surgical device 114 to store surgical images 132 of surgical procedures captured by the camera 128. The surgical images 132 can be stored as separate images or as one or more video files.

In the example shown in FIG. 1, surgical images 132 of a robotic surgical procedure captured by the camera 128 can also be transmitted to the surgeon console 104 and be displayed on a video monitor 108 in real time so that the surgeon 102 can view the procedure while the surgical tools 126 are being operated on the patient 130. In this example, the surgeon 102 can use the surgeon console 104 to control the surgical tools 126 and the camera 128. The surgeon 102 can use controls 106 on the surgeon console 104 to maneuver the surgical tools 126 and camera 128 by sending control signals 110 to the corresponding surgical tools 126 or camera 128.

For example, the surgeon 102 can move the camera 128 to various positions of patient body to find the proper operating site. The surgeon 102 can then move the camera 128 to a position where a surgical tool 126 to be used is located to bring the surgical tool 126 inside the field of view of the camera 128. The surgeon 102 may then move the surgical tool 126 along with the camera 128 to the operating site. For safety reasons, the robotic surgical system 100 will prevent the surgeon 102 from moving a surgical tool 126 if the surgical tool 126 is not in field of view of the camera 128. As a result, if a surgical tool 126 lies outside the field of view of the camera 128, the robotic surgical system 100 can disable the out-of-view surgical tool so that it cannot be moved or operated. Such a tool may be re-enabled when it is back in the camera view. Here, a tool is considered to be within the field of view of a camera if a substantial amount of the tool is within the field of view of the camera. In other words, if only a small portion, such as the tip of the tool, is within the camera view, it is still unsafe to allow the surgeon to operate the tool and thus the tool is not considered to be within the camera view. The amount of the tool that needs to be in the camera view in order to allow safe operation might be different for different types of tools.

Whether a surgical tool 126 is in the field of view of the camera 128 can be determined by determining the position of the surgical tool 126 relative to the camera 128. The robotic surgical device 114 can include a position predictor 118 to predict the position of the surgical tool 126. The prediction can be performed through a kinematic chain model of the robotic arm of the robotic surgical device 114 holding the surgical tool 126. The kinematic chain model can predict the position of the surgical tool 126 based on the dimensions and connectivity of the links and joints of the robotic arm. Information collected from various sensors deployed in the robotic arm, such as the direction and degree of a rotation occurred at a joint, can also be utilized to perform the prediction. In addition, computer aided design (CAD) models of the surgical tool can also be utilized to predict the position of the surgical tool.

Figure 2:
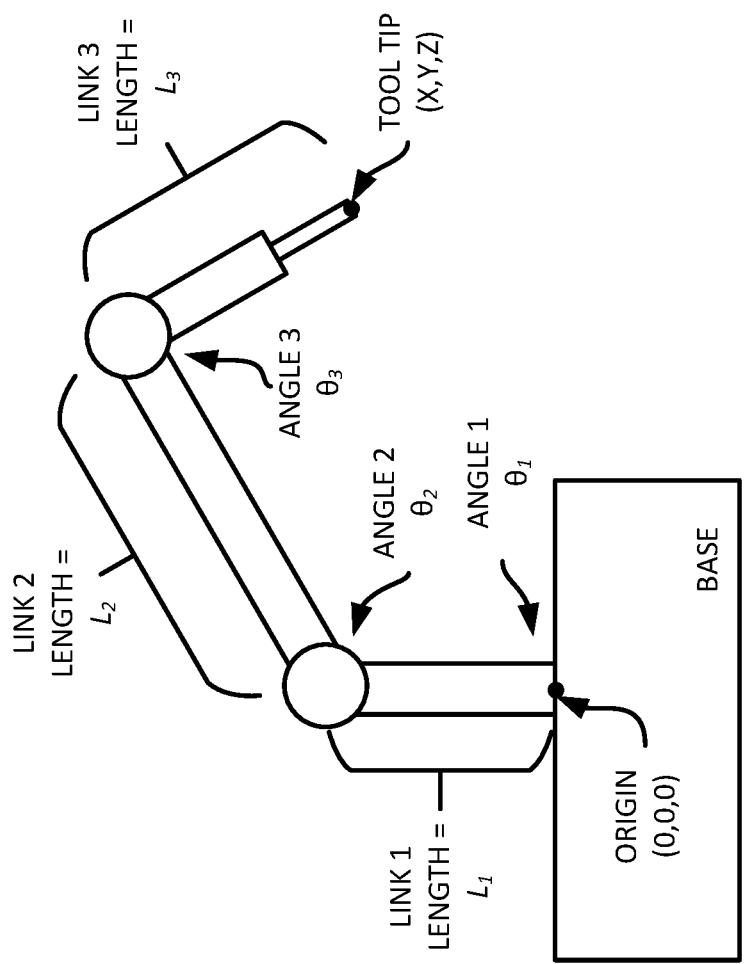
FIG. 2 shows an example kinematic chain model of a robotic arm holding a surgical tool that can be utilized to predict the position of the surgical tool.

FIG. 2 illustrates an example kinematic chain model for an robotic arm. In this example, the robotic arm includes three links, Link 1, Link 2 and Link 3, having respective lengths L1, L2 and L3. The three links are connected via two joints having respective angles $\theta_2$ and $\theta_3$. The base of the robotic arm and Link 1 form angle $\theta_1$. If the base of the robotic arm is used as the origin (0,0,0), the coordinates (X,Y,Z) of the position of the tool tip in the three-dimensional space can be determined based on the length of each of the three links, namely, L1, L2 and L3 and the values of angles $\theta_1$, $\theta_2$ and $\theta_3$. Similarly, the position of the camera 128 can be predicted by utilizing the kinematic chain model of the robotic arm holding the camera 128.

Once the positions and poses of the surgical tools 126 and the camera 128 are determined, the relative position of each surgical tool 126 with regard to the camera 128 can also be determined. In addition, the field of view of the camera 128 can be determined based on the parameters and settings of the camera 128, such as the lens and zooming information. Based on these types of information, it can be determined whether a surgical tool 126 is inside the field of view of the camera 128 and thus determining whether the surgical tools 126 should be disabled or not. The position predictor 118 can store the predicted position of the surgical tools 126 as well as other information about the surgical tools loaded by the tool controller 116, such as the type of each loaded tool, as the loaded tool information 122.

However, various errors, such as compliance errors and measurement errors, can cause the prediction of the position or pose of the surgical tools 126 and/or the camera 128 to be inaccurate. This problem is especially prominent when the robotic surgical device 114 have long robotic arms. In those cases, small deflections or errors in proximal joint measurements can become relatively large errors in predicted position or pose for the surgical tool 126 or the camera 128. As a result, a surgical tool 126 that is predicted to be inside the field of view of the camera 128 might be actually outside the camera view. Allowing the surgeon 102 to move or operate such a tool can cause unintentional injury to the patient 130. In addition, a surgical tool 126 that is predicted to be outside the field of view of the camera 128 might actually be visible through the camera 128. Disabling such an in-view surgical tool can cause frustration and confusion to the surgeon 102 since he is able to see the tool but not control it.

Figure 3A:
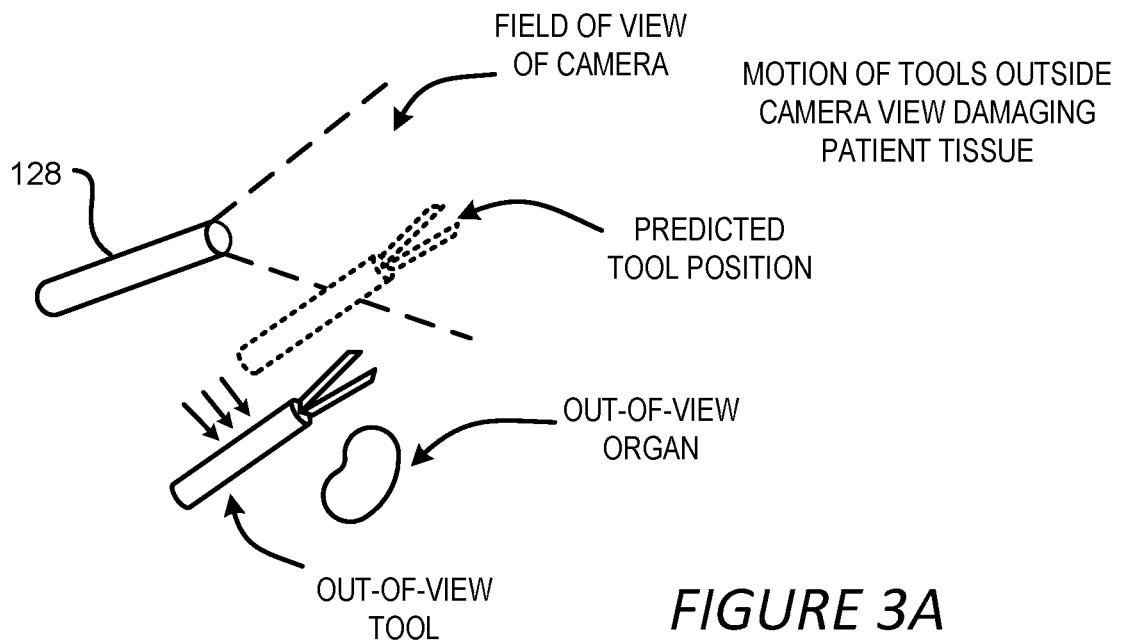
FIGS. 3A and 3B show example safety issues that can be addressed by the robotic surgery system with improved safety via video processing.

FIG. 3A illustrates one example of the problem caused by inaccurate position prediction of the surgical tool 126. In FIG. 3A, an out-of-view surgical tool is erroneously predicted to be inside the camera view. The surgeon 102 is able to operate the out-of-view tool, but unable to see it in the surgical images 132 displayed on the video monitor 108. As a result, the out-of-view surgical tool might damage the tissue or organ that is also outside the field of view of the camera 128 without the surgeon 102 realizing it.

Figure 3B:
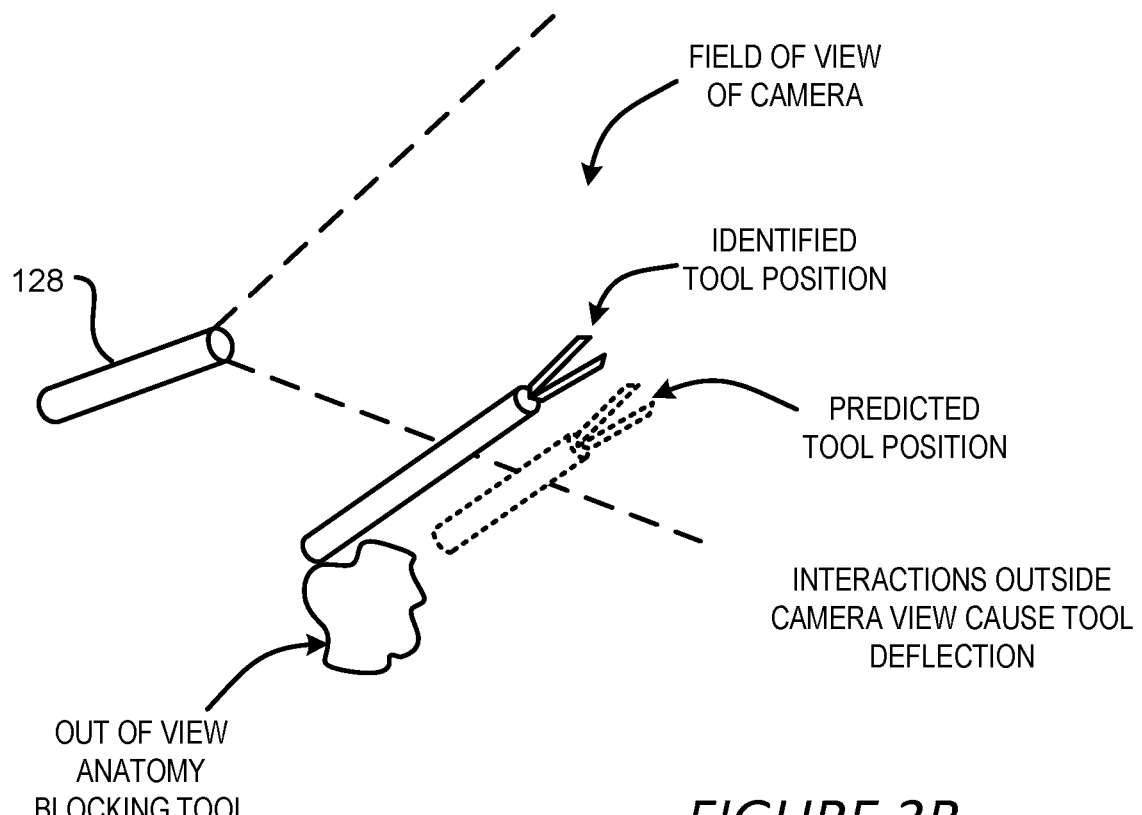

Furthermore, even if a tool is in the field of view of the camera 128, it is difficult for the surgeon 102 to know the amount of force applied by the surgical tool 126 to the patient's anatomy. Excessive amount of force applied on the patent 130 can cause deflection on the surgical tool 126 thereby resulting in the actual position of the surgical tool 126 to be different from the predicted position. FIG. 3B illustrates an example of this problem. In FIG. 3B, an in-view surgical tool is blocked by an out-of-view anatomy. The force applied by the surgical tool on the out-of-view anatomy deflects the surgical tool causing its position deviating from its predicted position. If the force deflecting the tool is large, it can cause injury to the patient 130. For example, the applied force may injure the out-of-view anatomy or it may cause significant deflection in the tool leading to undesired movement of the tool within the patient 130.

To improve the safety of robotic surgeries and to address the above problems, the robotic surgical device 114 can further include a safety module 120 according to the technologies disclosed herein. The safety module 120 can analyze the surgical images 132 captured during the surgical procedure to identify the position and pose of the surgical tools appeared in the surgical images 132. For example, stereo images taken by surgical endoscopes, which are typically stereo cameras, can be utilized to estimate depth information of the surgical tools more accurately thereby facilitating the detection of the position and pose of the surgical tool. Such information can be compared with the position information provided by the position predictor 118 to identify safety issues in the surgical procedure and provide safety instructions 136 to the robotic surgical device 114 to address those safety issues.

As used herein, the surgical images 132 can include one or more videos of the surgical procedure captured by the camera 128 or any individual images contained in such videos. The analysis can include identifying surgical tools 126 used in the surgical procedure from the surgical images 132, for example, through object recognition or other image/video processing techniques. The types of the identified surgical tools 134 can also be determined. The position and type information of the identified surgical tools 134 can then be compared with the loaded tool information 122 obtained from the position predictor 118 that corresponds to the analyzed surgical images 132 to determine if the identified surgical tools match the loaded surgical tools.

A match can be determined if the number and the types of the identified surgical tools are the same as the number and types of the loaded surgical tools as specified in the loaded tool information 122. If the number of the identified surgical tools is different from the number of the loaded surgical tools, the safety module 120 can further identify the loaded surgical tools that are not in the identified surgical tools. These tools represent the surgical tools that are predicted to be in the field of view of the camera, but missing from the surgical images 132. As discussed above, these out-of-view loaded surgical tools can cause damages to the patient and thus should be disabled. The safety module 120 can instruct the tool controller 116 to disable the out-of-view surgical tools. Disabling a surgical tool 126 can include, but is not limited to, preventing the input of the surgeon 102 from being sent to the surgical tool 126; deactivating energy applied by the surgical tool 126, e.g., for cauterizing tissue, locking the drive motors or joints to prevent movement of the surgical tool 126, and so on. Alternatively, or additionally, the safety module 120 can slow down the out-of-view surgical tools to reduce the risk of the injury caused by these tools.

Additionally, the safety module 120 can further determine surgical tools that are in the identified surgical tools, but not in the loaded surgical tools. These are the surgical tools that are predicted to be outside the field of view of the camera, but are visible in the surgical images 132. The safety module 120 can allow these surgical tools to be enabled, for example, by instructing the tool controller 116 to remove any mechanisms implemented when disabling the surgical tools so that they can be used by the surgeon 102 when needed. For example, enabling a surgical tool can include allowing the input of the surgeon 102 be sent to the surgical tool 126, activating energy applied by the surgical tool if necessary, unlocking the drive motors or joints to allow movement of the surgical tool and so on.

If the number of the tools in the loaded surgical tools and the identified surgical tools are the same, but the types of the surgical tools are different, it can be determined that a tool with a wrong type might have been loaded and used in the surgical procedure. The safety module 120 can similarly instruct the tool controller 116 to disable the unmatched surgical tools 126 to prevent injury or avoid further damage.

Even if the number and the types of the loaded surgical tools match those of the identified surgical tools, it is still possible that a surgical tool 126 is at a position different from its predicted position. Such a positional difference can be caused by the force exerted by the surgical tool 126 on patient issue deflecting the surgical tool 126. In those scenarios, the force of a surgical tool 126 can be estimated by the safety module 120 to determine whether the tool force is excessive and unsafe to the patient 130.

The tool force can be estimated by evaluating the difference between the positions and poses of the identified surgical tool and the corresponding loaded surgical tool. The difference in tool pose along with information such as the shape and materials of the tool and the robotic arm can be utilized to estimate the tool force. The estimated tool force can then be compared with a threshold value to determine if the force of the tool is excessive. If so, the safety module 120 can cause a warning message to be generated and transmitted to the surgeon 102 so that the surgeon 102 can take proper actions, such as moving the surgical tool to a different location, changing the pose of the surgical tool, or even retracting the surgical tool. Alternatively, or additionally, the safety module 120 can send a safety instruction to the tool controller 116 to move the surgical tool in a non-intruding position before disabling it. Additional details concerning the operations of the safety module 120 are provided below with regard to FIGS. 4-7.

It should be understood that although FIG. 1 illustrates the various modules, such as the safety module 120, the position predictor 118, the tool controller 116 and the datastore 124, are included in the robotic surgical device 114, one or more of these modules can be implemented in different ways within a robotic surgical system. For example, the functionality described above need not be separated into discrete modules, or some or all of such functionality may be located on a computing device separate from the robotic surgical device 114, such as a central controlling device connected to the robotic surgical device 114 directly or through a network and configured to control the operations of the robotic surgical system 100.

In addition, upon detecting a safety issue, such as an out-of-view surgical being predicted to be in view, or a tool with a wrong type is loaded, a perceivable indication can be provided so that the personnel in the operating room, including the surgeon 102, can be notified of the issue. For example, a vibration can be generated, a special sound can be played, or an LED light on the robotic surgical device 114 or other devices in the robotic surgical system 100 can be turned on to indicate the safety issue. A warning message or a highlight can be generated and presented on the video monitor 108 of the surgeon console 104 to draw the attention of the surgeon 102.

Furthermore, mechanisms can be implemented to enable the surgeon 102 or other authorized individuals to provide input to the safety check performed by the safety module 120. For example, a user interface can be designed and presented on the video monitor 108 along with the surgical images 132 to allow the surgeon 102 to flag certain surgical tools that will not be used by the surgeon 102 so that they can be ignored by the safety module 120. Other mechanisms can be implemented to receive inputs from the surgeon 102 or authorized individuals.

Figure 4:
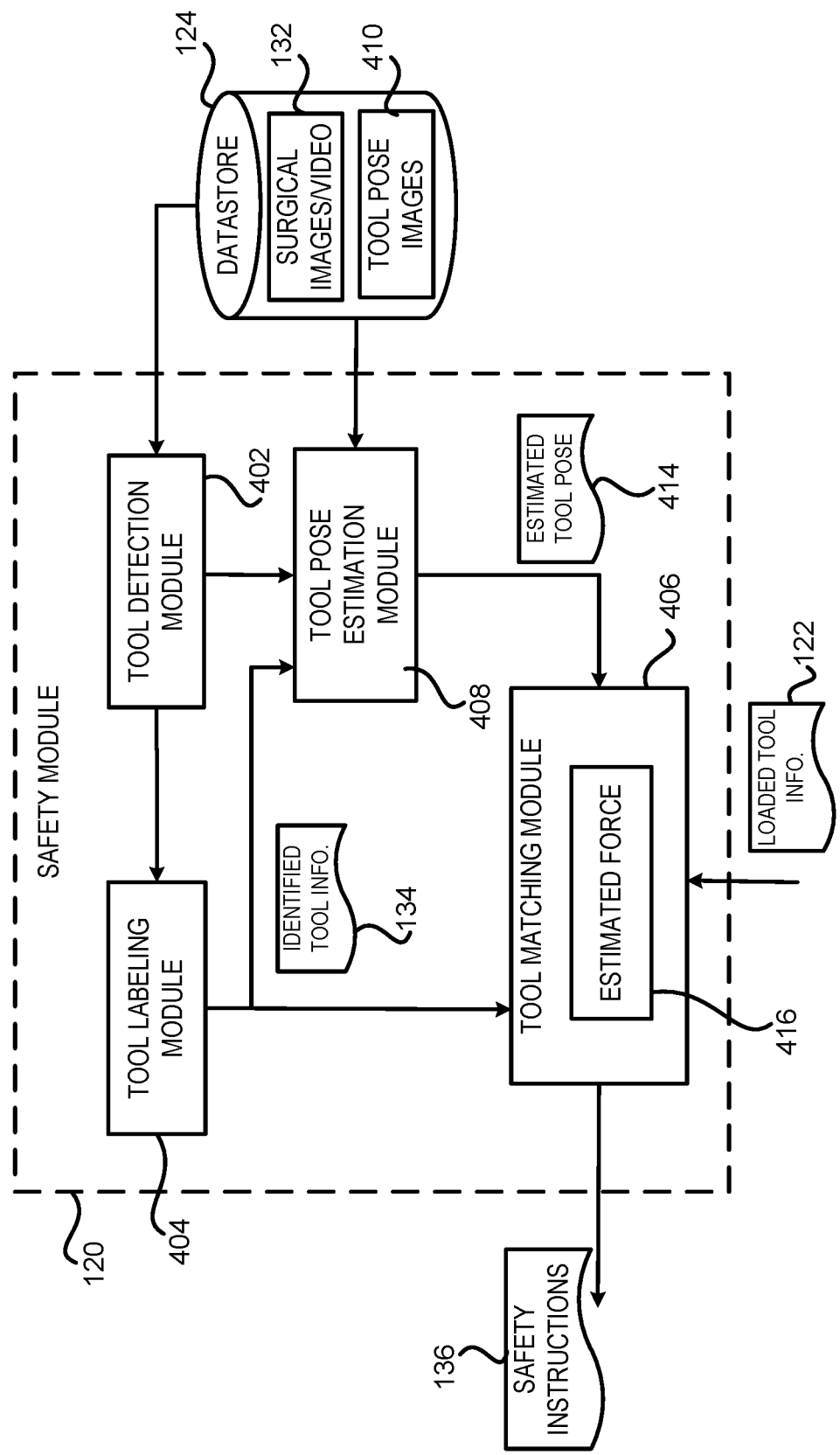
FIG. 4 shows a block diagram illustrating aspects of the safety module of the robotic surgery system with improved safety via video processing.

Referring now to FIG. 4 where a block diagram illustrating aspects of the safety module 120 of the robotic surgical system 100 is shown. FIG. 4 will be presented in conjunction with FIGS. 5A-5D where example simulated images of loaded surgical tools and identified surgical tools are shown.

As illustrated in FIG. 4, the safety module 120 can include a tool detection module 402 configured to detect the surgical tools captured in the surgical images 132. The detection of the tools can be performed by using object recognition or other image/video processing techniques.

For example, a trained machine-learning ("ML") technique, such as a convolutional neural network, can be trained and utilized to recognize surgical tools from images or videos. Although convolutional neural networks are described herein, any suitable ML technique may be trained to recognize different surgical tools from images or videos, such as a long short-term memory ("LSTM") technique, a dynamic time warping ("DTW") technique, a hidden Markov model ("HMM"), etc., or combinations of one or more of such techniques—e.g., CNN-LSTM, CNN-HMM or MCNN (Multi-Scale Convolutional Neural Network).

The convolutional neural network can be trained, or fine-tuned if the neural network is pre-trained, by using a set of training samples including surgical procedure images and corresponding labeling indicating whether a surgical tool exists in an image or not. After the training, the convolutional neural network can estimate whether a given image or a set of images contain surgical tools or not and, if so, where the surgical tools are positioned in the image.

The detected surgical tools can then be sent to a tool labeling module 304, where the types of the identified surgical tools can be recognized based on the surgical images 132 containing the detected surgical tools. The tool types can include, but are not limited to, tools for grasping for holding or retracting objects, such as forceps, graspers and retractors, tools for suturing and cutting, such as needle drivers, scalpels and scissors, and other tools that can be used during a surgery. Depending on the surgery being performed or to be performed, sub-type of the surgical tools can also be identified. For example, the tool labeling module 304 can identify a grasper tool as a fenestrated grasper for grasping delicate tissue like peritoneum and bowel, or a traumatic grasper for securing thicker tissue or organs.

Similar to the tool detection module 302, the tool labeling module 304 can employ machine learning or other object recognition techniques to estimate the tool type of the identified surgical tools. For example, a convolutional neural network can be used to recognize the tool type for each of the identified surgical tools. The convolutional neural network can be trained using training samples including images of surgical tools, computer-generated images based on CAD files for the tools and their respective tool types. The training convolutional network can be applied to the portion of the surgical images 132 that contain an identified surgical tool to predict the tool type for the identified surgical tool.

Alternatively, or additionally, identifying the tool type can be achieved through labeling the tool body. For example, a label or other visible identifier carrying a serial number or anything representing the identity of a surgical tool, such as a bar code or a quick response ("QR") code, can be affixed to the body of the surgical tool, such as the shaft of the surgical tool. The label can be identified from the surgical images 132 and the serial number can be recognized or interpreted from the identified label. The recognized serial number can then be utilized to, for example, query a database of surgical tools, to identify the corresponding tool type. Other types of identifiers may be employed as well, such as an RFID tag affixed to the surgical tool and positioned to be readable by the robotic surgical system, e.g., by affixing the RFID tag at a location near the base of the surgical tool.

It should be appreciated that the methods presented above for detecting the surgical tools and identifying the tool type from the surgical images 132 are for illustration only and should not be construed as limiting. Other methods can also be employed to facilitate the detection of the surgical too and the tool type. For instance, information obtained through imaging mechanisms other than the camera 128 can also be utilized to facilitate the identification of the surgical tools. These imaging mechanisms can include, but are not limited to, the ultrasound imaging, optical contrast imaging, fluorescent imaging and so on.

In one example, the camera 128 or the surgical tools 126 can be equipped with an ultrasound probe for detecting objects such as lung tumor in certain type of surgeries. The tool detection module 402 and/or the tool labeling module 404 can access the ultrasound images taken by the ultrasound probe to facilitate the detection of the surgical tool and the tool type. These additional imaging mechanisms can be especially helpful when the surgical tools 126 are hidden in the surgical images 132, for example, by anatomy tissue. The detected tools can be utilized to visualize the hidden tools, such as by outlining the specific tools in the surgical images 132, which can be beneficial for tasks such as find the one-to-one correspondence between the loaded surgical tools and the identified surgical tools as will be discussed below.

The position and type information of the identified surgical tools can then be sent to a tool matching module 406 to determine whether the information of the identified surgical tools match that of the loaded surgical tools determined by the position predictor 118. To facilitate the matching, a simulated camera image can be generated based on the positions of the identified surgical tools and the loaded surgical tools, the camera field of view and distortions. Example simulated camera images are shown in FIGS. 5A-5D, where both the identified surgical tools 504 estimated from the surgical images 132 and the loaded surgical tools 502 predicted by the position predictor 118 are shown. In these figures, the identified surgical tools 504 are illustrated in solid lines, and the loaded surgical tools 502 are illustrated in dotted lines.

In FIG. 5A, there are two identified surgical tools: a grasper 504A and a scalpel 504B, and two loaded surgical tools: a grasper 502A and a scalpel 502B. The tool matching module 406 can determine a one-to-one correspondence between the two sets of surgical tools. In some implementations, the correspondence can be determined by choosing tools with nearly matching positions in the simulated images and matching tool types. For example, the tool matching module 406 can determine that the position of the loaded surgical tool 502A is closer to the position of the identified surgical tool 504A than the identified surgical tool 504B, and that the type of the loaded surgical tool 502A matches that of the identified surgical tool 504A. The tool matching module 406 can thus determine that the identified surgical tool 504A and the loaded surgical tool 502A correspond to each other. Similarly, the tool matching module 406 can determine that the identified surgical tool 504B and the loaded surgical tool 502B correspond to each other because the position of the loaded surgical tool 502B is closer to the position of the identified surgical tool 504B than the identified surgical tool 504A and the type of the loaded surgical tool 502B matches that of the identified surgical tool 504B.

The difference between the positions of two surgical tools can be calculated, for example, as the Euclidean distance between center points of the two surgical tools. The center point of a surgical tool's end effector can be selected as the center of gravity of the surgical tool or any other points that can be used to represent a surgical tool consistently over the two sets of surgical tools. The difference between the types of two surgical tools can be converted to a quantity with a scale that is comparable to the distance between the positions of the two surgical tools. As a result, the problem of finding the one-to-one correspondence between the loaded surgical tools 502 and the identified surgical tools 504 can be formulated as an optimization problem such as follows:

$$\min_Q \sum_{(i,j) \in Q} \alpha_1 D(P_i, P_j) + \alpha_2 D(T_i, T_j) \quad (1)$$

where $D(P_i, P_j)$ is the difference between the position $P_i$ of the identified surgical tool i and the position $P_j$ of the loaded surgical tool j projected onto the imagining plane of the camera 128; $D(T_i, T_j)$ is the difference between the type $T_i$ of identified surgical tool i and the type $T_j$ of loaded surgical tool j. $\alpha_1$ and $\alpha_2$ are two parameters that can be utilized to adjust the relative importance between the positional difference and the tool type difference in the minimization problem. Q is a set containing a possible correspondence between the identified surgical tools 504 and the loaded surgical tools 502.

In the example shown in FIG. 5A, Q can be {(grasper 504A, grasper 502A), (scalpel 504B, scalpel 502B)}. That is, the identified grasper 504A corresponds to the loaded grasper 502A and the identified scalpel 504B corresponds to the loaded scalpel 502B. In this example, (i,j) in Equation (1) can take the value of (grasper 504A, grasper 502A) and (scalpel 504B, scalpel 502B) when calculating the difference $D(P_i, P_j)$ and $D(T_i, T_j)$. An alternative value for Q in the example shown in FIG. 5A can be {(scalpel 504B, grasper 502A), (grasper 504A, scalpel 502B)}, i.e. the identified scalpel 504B corresponds to the loaded grasper 502A and the identified grasper 504A corresponds to the loaded scalpel 502B. The optimization problem shown in Equation (1) can find the proper Q value, i.e. the proper correspondence between the identified surgical tools 504 and the loaded surgical tools 502, by minimizing the difference between the two sets of surgical tools.

Additional requirements can be added to help identify the correspondence between the loaded surgical tools 502 and the identified surgical tools 504. For example, relative position information, such as the grasper 504A (or 502A) should be on the left side of the scalpel 504B (or 502B), can be used to limit the possible correspondences between the two sets of surgical tools. These additional information can reduce the search space of Q and can be formulated as one or more constraints of the optimization problem in Equation (1). It should be understood that the optimization problem described above is merely for illustration purposes, and should not be construed as limiting. Various methods of finding the correspondence between the loaded surgical tools and the identified surgical tools can be utilized.

Alternatively, or additionally, a label or other visible identifier, such as a bar code or a QR code, representing an identification of a surgical tool can be affixed on the tool body. The identification of the surgical tools can be read on the identified surgical tools 504 from the surgical images 132 and interpreted to find the corresponding loaded surgical tool 502. If visible identifiers are available on tool body, the optimization process described above can be utilized to verify the correspondence determined through the identifier or be used when the tool identifier cannot be read reliably from the surgical images 132.

The example shown in FIG. 5A has the same number of identified surgical tools 504 and loaded surgical tools 502. It is, however, possible that the number of identified surgical tools 504 using the surgical images 132 is different from the number of loaded surgical tools 502 determined by the position predictor 118. In the example shown in FIG. 5B, there are two loaded surgical tools: a grasper 502C and a scissor 502D, but only one identified surgical tool: a grasper 504C. This can occur when the position predictor 118 mistakenly determine that the scissor tool 502D is in the field of view of the camera 128 when it is not. In this case, the tool matching module 406 can determine that the number of loaded surgical tools 502 and the identified surgical tools 504 do not match, and can perform further analysis to determine the unmatched surgical tool.

For example, the tool matching module 406 can first find out which of the loaded surgical tools 502C and 502D corresponds to the identified surgical tool 504C, for example, by formulating and solving the optimization problem of Equation (1) as discussed above. After identifying that the loaded surgical tool 502C corresponds to the identified surgical tool 504C, the tool matching module 406 can further retrieve information about the loaded surgical tool 502D that is missing from the surgical images 132. For instance, the tool matching module 406 can determine that the loaded surgical tool 502D is a scissor tool and is loaded on the second robotic arm of the robotic surgical device 114. Based on this information, the tool matching module 406 can demand that the surgical tool carried on the second robotic arm to be disabled, for example, by generating and sending safety instructions 136 to the tool controller 116. The tool controller 116 can disable the loaded surgical tool 502D by, for example, preventing user input from being sent to the surgical tool 502D; deactivating energy applied by the surgical tool 502D, or locking the drive motors or joints of the surgical tool 502D. In this way, the out-of-view scissor tool 502D cannot be moved and operated by the surgeon 102 until it is brought in the field of view of the camera 128, thereby preventing accidental injury to patient 130 by the scissor tool 502D. To move a tool, such as the out-of-view scissor tool 502D, into the field of view of the camera, the surgeon 102 can move the camera to the location of the tool and then move the tool along with the camera back to the operating site.

FIG. 5C also shows an example where the number of the loaded surgical tools 502 does not match the number of identified surgical tools 504. In this example, there are two identified surgical tools: a grasper 504E and a scissor 504F, and one loaded surgical tool: a grasper 502E. This can occur when the position predictor 118 mistakenly determined that the scissor tool is outside the field of view of the camera 128 and thereby disabled it preventing the surgeon from using it. Similar to the example shown in FIG. 5B, the tool matching module 406 can determine that the number of tools in the two sets of surgical tools does not match and further determine that the identified surgical tool 504E corresponds to the loaded surgical tool 502E. Regarding the identified surgical tool 504F, the tool matching module 406 can determine that the scissor tool corresponding to the identified surgical tool 504F is in the field of view of the camera 128 and is safe to use even though the position predictor 118 determines otherwise. As a result, the tool matching module 406 can instruct, via safety instruction 136, the tool controller 116 to enable the scissor tool. This can help to avoid the frustration and confusion of the surgeon 102 caused by the prediction error of the position predictor 118.

Sometimes, even if the number of loaded surgical tools 502 matches the number of the identified surgical tools 504, there can still be problems with the surgical tools loaded by the robotic surgical device 114. FIG. 5D illustrates such an example. In FIG. 5D, both the loaded surgical tools 502 and the identified surgical tools 504 have two tools. However, the two tools that are close in position have different tool types, i.e. the loaded surgical tool 502G is a grasper tool and the identified surgical tool 504G is a scissor tool. One possible reason for this is that the tool controller 116 has loaded a wrong tool on the robotic arm. This can cause a serious problem in the surgery procedure, especially when the shapes of the wrong tool and the correct tool are similar and the surgeon cannot immediately recognize the difference in the surgical images 132 shown on the video monitor 108. Once the tool type mismatch is detected, the tool matching module 406 can generate a safety instruction 136 to disable the wrongly loaded surgical tool and provide a warning to the surgeon 102.

As shown in FIG. 5A, even if the number of tools and the tool types between the loaded surgical tools and the identified surgical tools match, there can be discrepancy between the pose of an identified surgical tool 504A and the pose of the corresponding loaded surgical tool 502A. As discussed above with respect to FIG. 3B, such a discrepancy can be the result of deflection on the surgical tool caused by forces unknown to the position predictor 118. If the discrepancy is large, it can mean that an excessive force has been applied by the surgical tool on the patient body without the surgeon realizing it. To address this problem, the safety module 120 can include a tool pose estimation module 408 to estimate the tool pose of the identified surgical tools 504 relative to the camera 128. Such estimated tool pose of a surgical tool can be compared with a predicted tool pose of the surgical tool. The difference between the estimated and predicted tool pose can be utilized to determine the amount of forces applied by the surgical tool causing the deflection of the tool.

The tool pose estimation can be performed based on the surgical images 132. For example, object recognition techniques can be utilized to identify the pose of a surgical tool in the image, including the position of the surgical tool and the orientation of the surgical tool relative to the camera in a three-dimensional space. For example, a neural network trained to recognize the surgical tool and the pose of the surgical tool can be utilized to identify the tool pose. Alternatively, or additionally, the tool pose estimation module 408 can determine the pose of an identified surgical tool 504 by comparing the identified surgical tool 504 to a datastore 410 containing images of surgical tools in various poses. The tool pose can be determined if there is a match between the image of the identified surgical tool 504 and an image in the datastore 410.

In addition to estimate the tool pose using the two-dimensional images, the knowledge of the tool type and the tool geometry, such as the shaft width or head length, can be utilized to estimate the depth of the surgical tool relative to the camera 128 so that the tool pose in the three-dimensional space can be determined. Furthermore, in scenarios where the camera 128 is a stereoscopic camera or the robotic surgical device 114 is equipped with a stereoscopic camera, the depth information of the surgical tool can be estimated via triangulation of corresponding pixels on the stereo images. Additional fiducials could also be added to the tool shaft to give visual reference points for measurement. For example, a mark or other type of labels, can be added on the tool shaft for every centimeter to provide a visual reference points for the estimation of the tool pose. Various other methods can be utilized to estimate the pose of the identified surgical tools 134 in the surgical images 132.

The estimated pose 414 of the identified surgical tools 504 can then to be sent to the tool matching module 406 to estimate the force exerted by the surgical tool. The tool matching module 406 can compare the estimated pose 414 of a identified surgical tool 504 with a predicted pose of a corresponding loaded surgical tool 502. As discussed above, a kinematic chain model of the robotic arm holding the loaded surgical tool 502 and a kinematic chain model of the robotic arm holding the camera 128 can be utilized to predicted the pose of the loaded surgical tool 502. Through the comparison, the tool matching module 406 can calculate the difference between the estimated tool pose 414 and the predicted tool pose.

The tool matching module 406 can then estimate the force of the surgical tool based on the difference between the estimated and actual tool poses as well as other information, such as the stiffness of the surgical tool and the associated robotic arm, the location of the applied force along the kinematic chain. The stiffness of the surgical tool and the robotic arm can be determined by the geometry and materials of the surgical tool and the robotic arm holding the surgical tool. The analysis can be performed for each of the identified surgical tools in the field of view of the camera that have a corresponding loaded surgical tool 502. It should be noted that this estimation is based on an assumption that the difference in the tool poses of an identified surgical tool 504 and its corresponding loaded surgical tool 502 is the result of tool forces deflecting the surgical tool. If the deflection, thus the tool pose difference, is observed for all the surgical tools under analysis, it is likely that the camera 128 has been deflected causing the global effect of common deflection on all surgical tools. In that case, the effect of the camera deflection can be subtracted from the tool pose estimation of the identified surgical tool 504 when estimating the tool force.

The estimated force of the surgical tool can then be compared with a force threshold. If the estimated force is larger than a threshold, the tool matching module 406 can generate a warning message to notify the surgeon 102 about the excessive tool force. For example, the surgical tool that is exerting excessive force can be flagged or highlighted in the surgical images 132 shown on the video monitor 108. If the estimated force is too excessive, such as higher than an even higher force threshold, the tool matching module 406 can cause the robotic surgical device 114 to be paused, for example, by sending the safety instructions 136 to the tool controller 116 to request pausing the robotic surgical device 114 to temporarily preventing the surgical procedure to continue. The robotic surgical device 114 can resume its normal operations after the surgical tool exerting highly excessive force is withdrawn, moved to another position, or changed in other ways to reduce its force, such as via a reduction in proximal motor torques.

It should be understood that while the above process describes simulated camera images, such as those shown in FIGS. 5A-5D, generating these simulated camera images are optional and the technology described herein does not require those simulated images.

Figure 6:
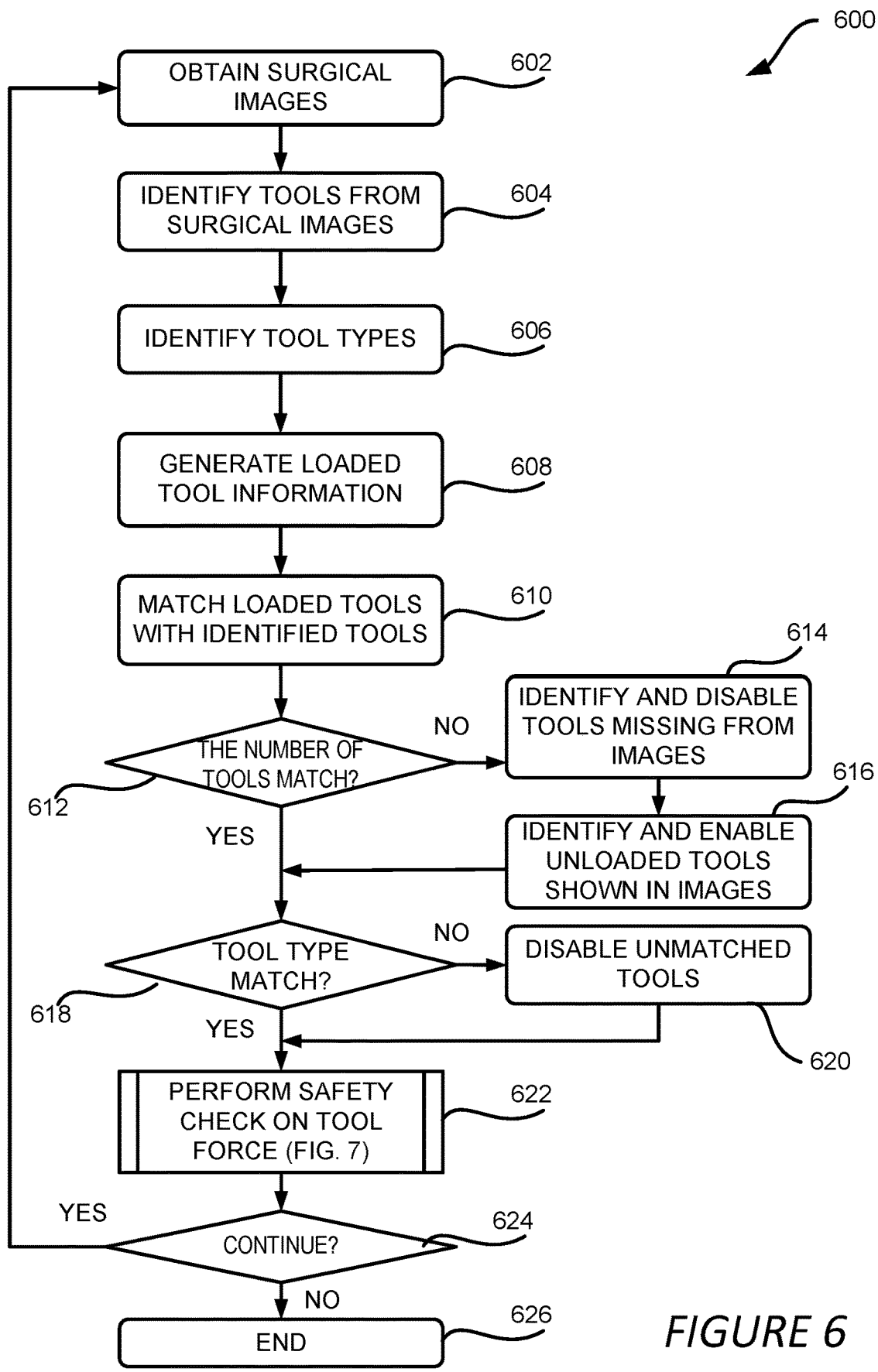
FIG. 6 shows an example method for improving robotic surgical safety via video processing.

Referring now to FIG. 6, where an example method 600 improving robotic surgical safety via video processing is presented. The example method 600 will be discussed with respect to the example system 100 shown in FIG. 1, but may be employed according to any suitable system according to this disclosure.

At block 602, the safety module 120 obtains or accesses surgical images 132 of an ongoing surgical procedure from, for example, from a real-time video feed from an endoscopic camera 128.

At block 604, the safety module 120 identifies surgical tools used in the surgical procedure using the surgical images 132. As discussed above, the identification can be performed using trained ML techniques or other object recognition or image/video processing techniques. In one example, the identification of the surgical tool can be performed by applying a convolutional neural network trained for recognizing surgical tools from images or videos onto the surgical images 132. The output of the neural network can indicate whether a surgical image 132 or a group of surgical images 132 contain surgical tools and if so, the positions of the surgical tools in the two-dimension surgical images 132.

In addition to the surgical images 132, other imaging mechanisms can be utilized to facilitate the identification of surgical tools in the surgical images 132, such as ultrasound imaging, optical contrast imaging, fluorescent imaging and so on. These additional imaging mechanism can be useful to identify surgical tools when they are not easily recognized from the 132, such as being blurred or be hidden by the patient tissue.

The identified surgical tools can then be analyzed to identify the types of the respective identified surgical tools at block 606. The tool type can be determined by employing a neural network training to recognize various types of surgical tools. Images or image patches containing surgical tools can be feed into the neural network and the output of the neural network can indicate the type of the surgical tool contained in the input image. For example, the neural network can be trained and utilized to determine the tool types including, but not limited to, tools for grasping for holding or retracting objects, such as forceps, graspers and retractors, tools for suturing and cutting, such as needle drivers, scalpels and scissors, and other tools that can be used during a surgery. Depending on how the neural network is trained, it can also be utilized to identify sub-types of the surgical tools. For example, the neural network can be utilized to identify a grasper tool as a fenestrated grasper for grasping delicate tissue like peritoneum and bowel, or a traumatic grasper for securing thicker tissue or organs.

In some scenarios, some of the surgical tools can have a label or other visible identifier affixed to the tool body, such as the shaft of the surgical tool. If the label can be recognized from the surgical images 132, then the surgical tools and their respective tool types can be identified by interpreting the label and referencing to a surgical tool database.

At block 608, the position predictor 118 can generate the loaded tool information 122 including the types, positions/poses and other information of the loaded surgical tools 502 at the time when the surgical images 132 are captured. The position predictor 118 can obtain data about the loaded surgical tools 502, such as the tool types and the robotic arms for the respective loaded surgical tool 502, from the tool controller 116. Such information may be provided when each of the surgical tools is loaded in the robotic surgical system 100, or may be obtained based on one or more identifiers provided on the surgical tool(s). Based on the information, the position predictor 118 can predict the position and pose of each loaded surgical tool 502 with respect to the camera 128 based on a kinematic chain model of the robotic arm holding the corresponding surgical tool and a kinematic chain model of the robotic arm holding the camera 128. The predicted three-dimension pose information of a loaded surgical tool 502 can be transformed into a two-dimensional position information of the loaded surgical tool 502 by projecting the position and pose information onto the imaging plane of the camera 128 so that the position of the loaded surgical tool 502 can be compared with the position of the identified surgical tool 504 in the surgical images 132. The predicted pose and/or position of the loaded surgical tools 502 can be included in the loaded tool information 122 along with the tool types and be sent to the safety module 120 for comparison.

At block 610, the safety module 120 tries to determine a one-to-one correspondence between the loaded surgical tools 502 and the identified surgical tools 504. As discussed above in detail, the correspondence can be determined by solving an optimization problem, such as that formulated in Equation (1), through iterative operations to find a set of correspondence between the two sets of surgical tools that minimize the overall distance between the loaded surgical tools 502 and the identified surgical tools 504. Various other methods for find the correspondence can also be utilized.

After finding the correspondence, the safety module 120 can determine, at block 612, whether the number of loaded surgical tools 502 matches the number of the identified surgical tool 504. If the two numbers do not match, the safety module 120 can identify those loaded surgical tools 502 that are not in the identified surgical tools 504. These tools can potentially cause injuries to patient because they can be operated by the surgeon 102 but are not in the field of view of the camera 128. The safety module 120 can thus instruct the tool controller 116 to disable these tools.

At block 616, the safety module 120 also identifies those tools that are in identified surgical tool 504 but are not in the loaded surgical tool 502. These tools can cause confusion and frustration of the surgeon 102 because they are in the field of view of the camera 128 but are disabled because they are predicted to be outside the camera view by the position predictor 118. The safety module 120 can instruct the tool controller 116 to enable these tools so that surgeon 102 can use them when needed.

For those loaded surgical tool 502 that have a corresponding identified surgical tool 504, the safety module 120 further determines, at block 618, if the type of loaded surgical tool 502 matches the type of its corresponding identified surgical tool 504. If the tool type does not match, the safety module 120 can instruct the tool controller 116 to disable the loaded surgical tool 502 because it is likely that a wrong surgical tool has been loaded. For the rest of the loaded surgical tools 502, i.e. loaded surgical tools 502 that have a corresponding identified surgical tool 504 with a matching tool type, the safety module 120 can perform a safety check on the tool force at block 622 to determine if any excessive force has been applied by the loaded surgical tool 502. Details regarding the operations at block 622 will be presented below with respect to FIG. 7.

At block 624, the safety module 120 determines if it will continue to monitor the safety of the robotic surgical device 114. If so, the safety module 120 repeats the method as described above for a next period of time of the surgical procedure. If not, the method ends at block 626.

It should be appreciated that the description of the method 600 of FIG. 6 is merely one example sequence, and that one or more blocks of the method 600 may be performed in different orders or may be omitted entirely. For example, generating the loaded tool information 122 at block 608 can be performed in parallel with the identification of the identified surgical tool 504 at blocks 602-606. In another example, the safety module 120 may omit the safety check on tool force in block 622, for example, in order to speed up the process so that a real-time safety feedback can be provided.

Figure 7:
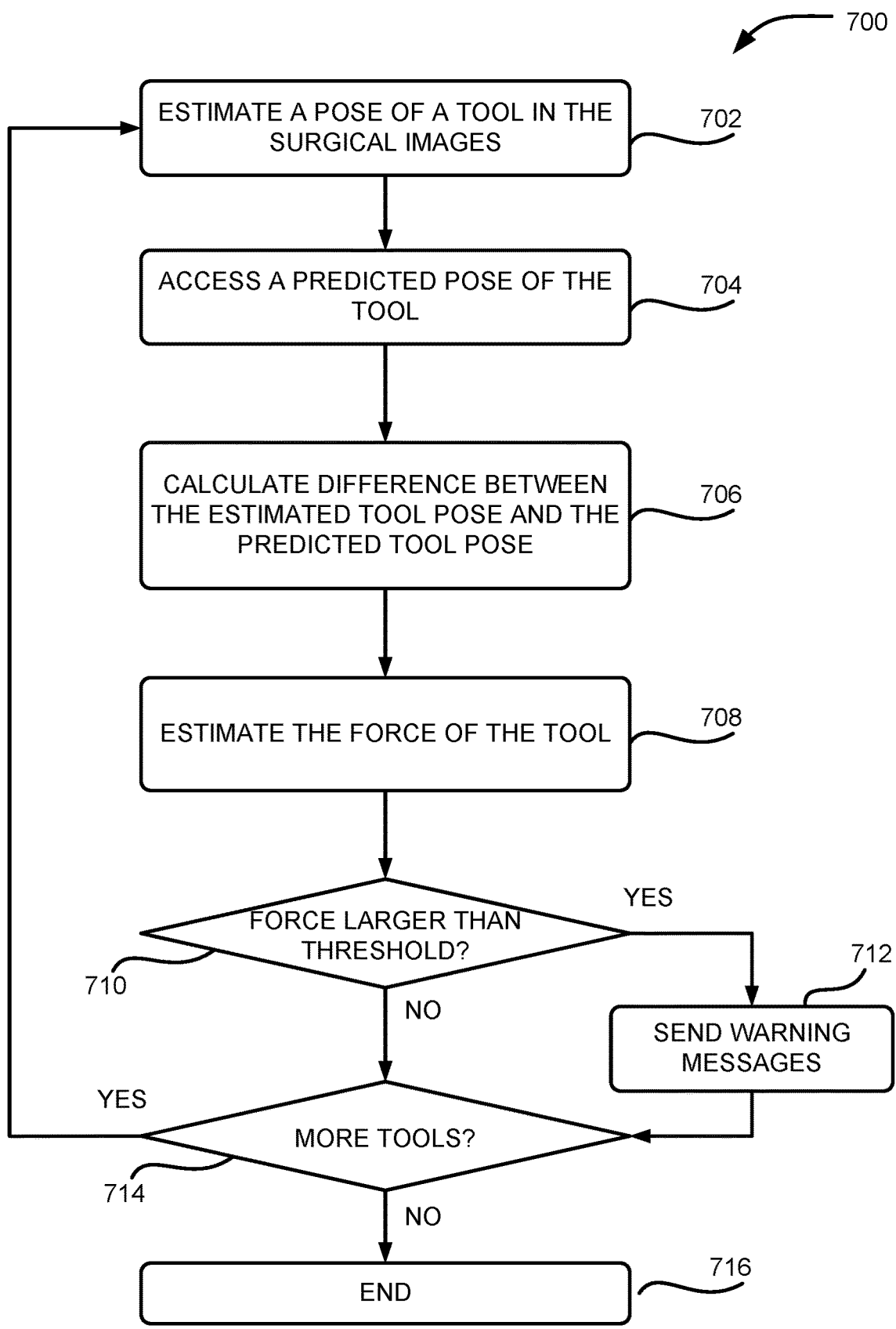
FIG. 7 shows an example method for estimating tool force in a robotic surgery system with improved safety via video processing.

Referring now to FIG. 7, where an example method 700 for estimating the force exerted by a surgical tool is illustrated. The example method 700 will be discussed with respect to the example system 100 shown in FIG. 1, but may be employed according to any suitable system according to this disclosure. At block 702, the safety module 120 estimates the pose of an identified surgical tool 504 in the surgical images 132. As discussed above, a pose of a surgical tool includes the position of the surgical tool and the orientation of the surgical tool relative to the camera in a three-dimensional space. The estimation of the pose can be performed by applying one or more trained ML techniques or other object recognition techniques on the surgical images 132, such as by using a neural network model trained to recognize surgical tool poses. Alternatively, or additionally, the pose of an identified surgical tool 504 can be determined by comparing the identified surgical tool 504 to a datastore 410 containing images of surgical tools in various poses. Other methods and information can also be utilized to determine the pose of the identified surgical tool 504 in the three dimensional space, such as the tool type and the tool geometry, stereo images of the tool, and so on.

At block 704, the safety module 120 can access the pose of the loaded surgical tool 502 that is predicted by the position predictor 118 as described in block 608 of the method 600. Then at block 706, the safety module 120 calculates the difference between the estimated pose of the identified surgical tool 504 and the predicted pose of the loaded surgical tool 502. Such a difference is then utilized to determine the tool force excreted by the loaded surgical tool 502 at block 708. As discussed above, the difference in the tool poses of the loaded surgical tool 502 and identified surgical tool 504 can be the result of the force deflecting the loaded surgical tool 502. As such, the difference in tool poses, along with other information such as the stiffness of the tool, can be utilized to determine that force that caused the tool deflection.

At block 710, the estimated tool force is compared with a force threshold. If the estimated tool force is higher than the force threshold, a warning message can be generated and sent to the surgeon 102 at block 712 to notify him to take proper actions to reduce the tool force. At block 714, the safety module 120 determines if there are more loaded surgical tools 502 for which the tool force is to be estimated. If yes, the safety module 120 repeats the method 700 as described above. If no more loaded surgical tools 502 to be analyzed, method 700 ends at block 716.

It should be appreciated that while the blocks of the method 1500 are depicted and described in a particular order, no such ordering is required. For example, blocks 702 and 704 may be performed in any order or substantially simultaneously. In addition, the force estimation for different loaded surgical tools 502 can be determined substantially simultaneously.

Figure 8:
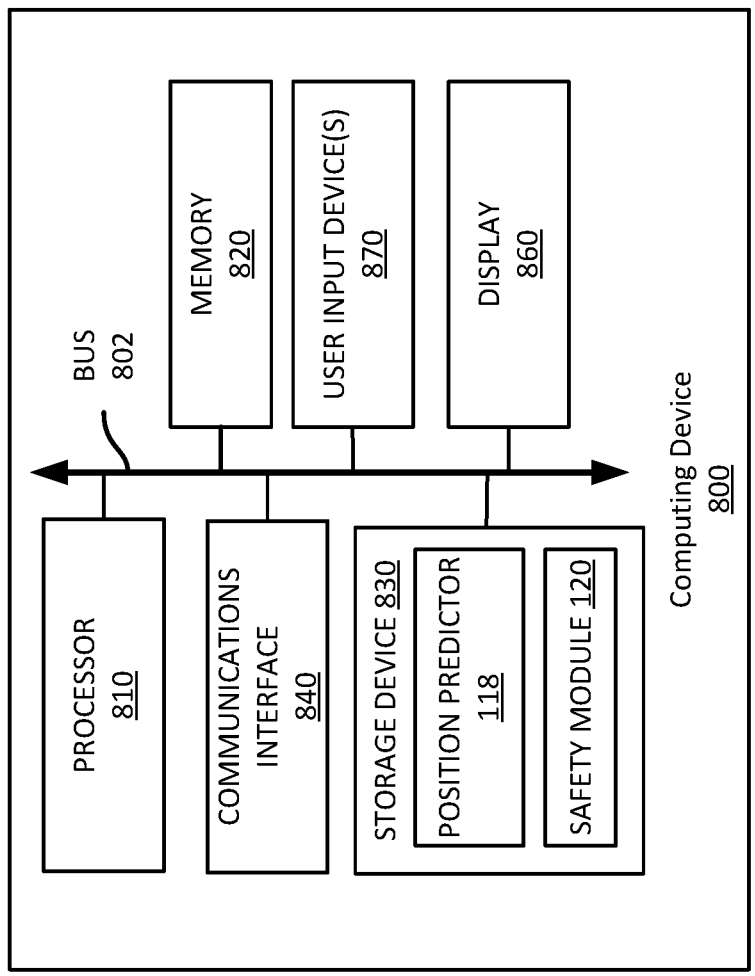
FIG. 8 shows an example computing device suitable for implementing aspects of the techniques and technologies presented herein.

Referring now to FIG. 8, FIG. 8 shows an example computing device 800 suitable for use in example systems or methods for improving robotic surgical safety via video processing. The example computing device 800 includes a processor 810 which is in communication with the memory 820 and other components of the computing device 800 using one or more communications buses 802. The processor 810 is configured to execute processor-executable instructions stored in the memory 820 to perform security check of the robotic surgical device 114 according to different examples, such as part or all of the example methods 600, 700 described above with respect to FIGS. 6 and 7. The computing device, in this example, also includes one or more user input devices 870, such as a keyboard, mouse, touchscreen, microphone, etc., to accept user input. The computing device 800 also includes a 860 display to provide visual output to a user.

The computing device 800 can include or be connected to one or more storage devices 830 that provides non-volatile storage for the computing device 800. The storage devices 830 can store system or application programs and data utilized by the computing device 800, such as modules implementing the functionalities provided by the safety module 120 and the position predictor 118. The storage devices 730 might also store other programs and data not specifically identified herein.

The computing device 800 also includes a communications interface 840. In some examples, the communications interface 840 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
    identifying, during a robotic surgical procedure, one or more surgical tools using one or more images of the robotic surgical procedure captured by a camera, the robotic surgical procedure employing a robotic surgical device controlling the one or more identified surgical tools;
    predicting, for at least one of the one or more images, one or more loaded surgical tools that are controlled by the robotic surgical device and should be in a field of view of the camera;
    comparing the one or more identified surgical tools with the one or more loaded surgical tools;
    determining that at least one of the one or more loaded surgical tools does not match any of the one or more identified surgical tools; and
    causing the at least one loaded tool of the robotic surgical device to be disabled.

2. The method of claim 1, wherein identifying the one or more surgical tools using the one or more images comprises:
    estimating a position of each of the one or more identified surgical tools; and
    recognizing a type of each of the one or more surgical tools using the one or more images.

3. The method of claim 2, wherein comparing the one or more identified surgical tools with the one or more loaded surgical tools comprises determining a correspondence between the identified surgical tools with the loaded surgical tools based, at least in part, upon the estimated positions of the identified surgical tools and predicted positions of the loaded surgical tools.

4. The method of claim 3, wherein the predicted positions of the loaded surgical tools are obtained based, at least in part, upon a kinematic chain model of the robotic surgical device.

5. The method of claim 3, wherein determining that at least one of the one or more loaded surgical tools does not match any of the one or more identified surgical tools comprises determining that the at least one loaded surgical tool has no correspondence in the one or more identified surgical tools.

6. The method of claim 3, wherein determining that at least one of the loaded surgical tools does not match any of the one or more identified surgical tools comprises determining that a type of the at least one loaded surgical tool is different from a type of a corresponding tool in the one or more identified surgical tools.

7. The method of claim 1, wherein identifying the one or more surgical tools from the one or more images comprises:
identifying one or more identifiers visible from the one or more images; and
interpreting the one or more identifiers to identify the one or more surgical tools.

8. The method of claim 1, further comprising:
determining that at least one of the identified surgical tools has no correspondence in the one or more loaded surgical tools; and
causing the at least one identified surgical tool to be enabled.

9. A robotic surgical device comprising:
a processor;
a camera; and
a non-transitory computer-readable medium having processor-executable instructions stored thereupon, which, when executed by the processor, cause the processor to:
identify, using one or more images of a surgical procedure captured by the camera during a robotic surgical procedure, one or more surgical tools used in the surgical procedure;
predict, for at least one of the one or more images, one or more loaded surgical tools that are loaded during the surgical procedure and should be in a field of view of the camera;
compare the one or more identified surgical tools with the one or more loaded surgical tools;
determine that at least one of the one or more loaded surgical tools does not match any of the one or more identified surgical tools; and
cause the at least one loaded surgical tool of the robotic surgical device to be disabled.

10. The robotic surgical device of claim 9, wherein identifying the one or more surgical tools using the one or more images comprises estimating a position of each of the one or more identified surgical tools.

11. The robotic surgical device of claim 9, wherein determining that at least one of the one or more loaded surgical tools does not match any of the one or more identified surgical tools comprises determining that the at least one loaded surgical tool has no correspondence in the one or more identified surgical tools.

12. The robotic surgical device of claim 9, wherein identifying the one or more surgical tools using the one or more images comprises recognizing a type of each of the one or more surgical tools using the one or more images.

13. The robotic surgical device of claim 9, wherein determining that at least one of the loaded surgical tools does not match any of the one or more identified surgical tools comprises determining that a type of the at least one loaded surgical tool is different from a type of a corresponding tool in the one or more identified surgical tools.

14. A non-transitory computer-readable medium comprising processor-executable instructions to cause a processor to:
identify, during a robotic surgical procedure, one or more surgical tools using one or more images of the robotic surgical procedure captured by a camera, the robotic surgical procedure employing a robotic surgical device controlling the one or more identified surgical tools;
predict, for at least one of the one or more images, one or more loaded surgical tools that are controlled by the robotic surgical device and should be in a field of view of the camera;
compare the one or more identified surgical tools with the one or more loaded surgical tools;
determine that at least one of the one or more loaded surgical tools does not match any of the one or more identified surgical tools; and
cause the at least one loaded surgical tool of the robotic surgical device to be disabled.

15. The non-transitory computer-readable medium of claim 14, wherein identifying the one or more surgical tools using the one or more images comprises estimating a position of each of the one or more identified surgical tools.

16. The non-transitory computer-readable medium of claim 14, wherein determining that at least one of the one or more loaded surgical tools does not match any of the one or more identified surgical tools comprises determining that the at least one loaded surgical tool has no correspondence in the one or more identified surgical tools.

17. The non-transitory computer-readable medium of claim 14, wherein determining that at least one of the loaded surgical tools does not match any of the one or more identified surgical tools comprises determining that a type of the at least one loaded surgical tool is different from a type of a corresponding tool in the one or more identified surgical tools.

* * * * *